(12) United States Patent
Veroux

(10) Patent No.: US 10,952,839 B2
(45) Date of Patent: Mar. 23, 2021

(54) VENOUS ENDOLUMINAL DEVICES FOR THE TREATMENT OF DEFECTS OF VEINS

(71) Applicant: Pierfrancesco Veroux, Catania (IT)

(72) Inventor: Pierfrancesco Veroux, Catania (IT)

( * ) Notice: Subject to any disclaimer, the term of this patent is extended or adjusted under 35 U.S.C. 154(b) by 348 days.

(21) Appl. No.: 14/439,233

(22) PCT Filed: Jul. 31, 2013

(86) PCT No.: PCT/IB2013/056283
§ 371 (c)(1),
(2) Date: Apr. 29, 2015

(87) PCT Pub. No.: WO2014/068412
PCT Pub. Date: May 8, 2014

(65) Prior Publication Data
US 2015/0289966 A1    Oct. 15, 2015

(30) Foreign Application Priority Data

Oct. 30, 2012  (IT) .............................. BS2012A0154
May 30, 2013  (IT) .............................. BS2013A0080

(51) Int. Cl.
*A61F 2/07*   (2013.01)
*A61F 2/82*   (2013.01)
*A61F 2/844*  (2013.01)

(52) U.S. Cl.
CPC .................. *A61F 2/07* (2013.01); *A61F 2/82* (2013.01); *A61F 2/844* (2013.01);
(Continued)

(58) Field of Classification Search
CPC .... A61F 2/07; A61F 2/82; A61F 2/821; A61F 2/823; A61F 2/825; A61F 2/826;
(Continued)

(56) References Cited

U.S. PATENT DOCUMENTS 6,010,530 A   1/2000   Goicoechea
6,623,521 B2  9/2003   Steinke et al.
(Continued)

FOREIGN PATENT DOCUMENTS

EP    0856300 A1   8/1998
WO    0028922 A1   5/2000
(Continued)

OTHER PUBLICATIONS

Your Dictionary, Definition of "stent", 2008, yourdictionary.com/stent (Year: 2008).*
(Continued)

*Primary Examiner* — Todd J Scherbel
*Assistant Examiner* — Mikail A Mannan
(74) *Attorney, Agent, or Firm* — Merchant & Gould P.C.

(57) ABSTRACT

Venous endoluminal devices, in particular for the treatment of defects of the veins, are provided with a substantially tubular body which defines an inner lumen and support modules oriented longitudinally and joined, in a distal direction, by distal bridges and in a proximal direction, by proximal bridges. Each support module includes a distal section, extending in a distal direction beyond the distal bridges, wherein the distal section is at least partially projecting in a radial direction, internally in relation to the inner lumen of the body. Methods of treatment using such devices are also provided.

23 Claims, 5 Drawing Sheets

(52) U.S. Cl.
CPC . *A61F 2002/828* (2013.01); *A61F 2250/0037* (2013.01); *A61F 2250/0039* (2013.01)

(58) Field of Classification Search
CPC ...... A61F 2/828; A61F 2/92; A61F 2002/072; A61F 2002/075; A61F 2002/077; A61F 2002/91583; A61F 2/2475; A61F 2230/0013; A61F 2230/0006; A61F 2230/0008; A61F 2230/0015; A61F 2230/0067; A61F 2230/0076; A61F 2230/0078; A61F 2230/0093; A61F 2/89; A61F 2/852; A61F 2/915; A61F 2002/91558; A61F 2002/91525; A61F 2002/91533
USPC ........................................................ 623/1.24
See application file for complete search history.

(56) References Cited

U.S. PATENT DOCUMENTS

| | | | |
|---|---|---|---|
| 2004/0015230 A1* | 1/2004 | Moll | A61F 2/2412 623/1.24 |
| 2008/0183280 A1* | 7/2008 | Agnew | A61F 2/2418 623/1.24 |
| 2010/0094411 A1* | 4/2010 | Tuval | A61F 2/2418 623/2.1 |
| 2011/0306916 A1* | 12/2011 | Nitzan | A61F 2/2418 604/9 |
| 2012/0046731 A1 | 2/2012 | Von Oepen et al. | |
| 2012/0130468 A1 | 5/2012 | Khosravi et al. | |
| 2012/0271396 A1* | 10/2012 | Zheng | A61F 2/82 623/1.2 |

FOREIGN PATENT DOCUMENTS

| | | | |
|---|---|---|---|
| WO | 2010128311 A1 | 11/2010 | |
| WO | WO-2012164295 A1 * | 12/2012 | A61F 2/966 |

OTHER PUBLICATIONS

The Free Dictionary, Definition of "hourglass", 2006, thefreedictionary.com/hourglass (Year: 2006).*

* cited by examiner

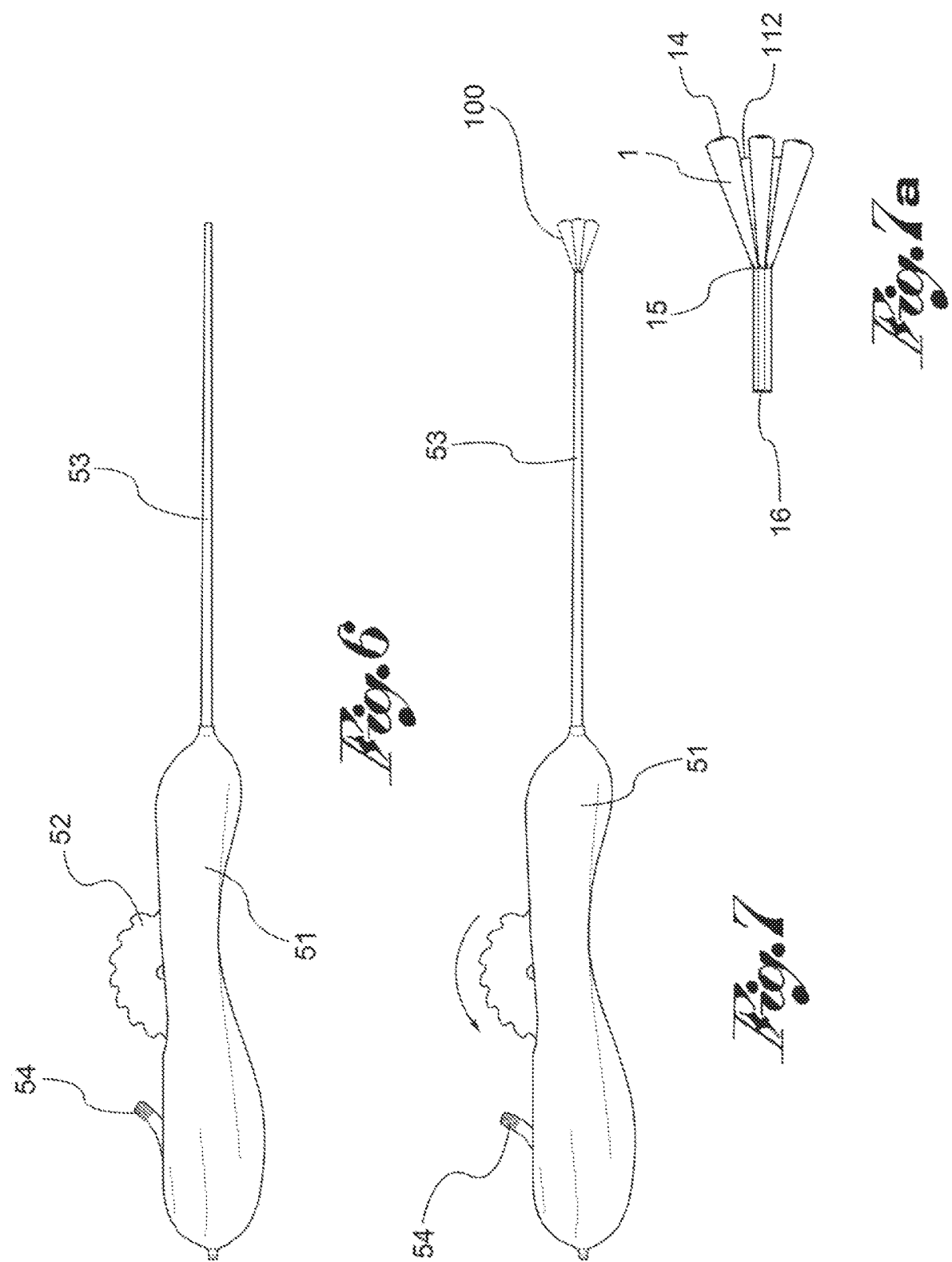

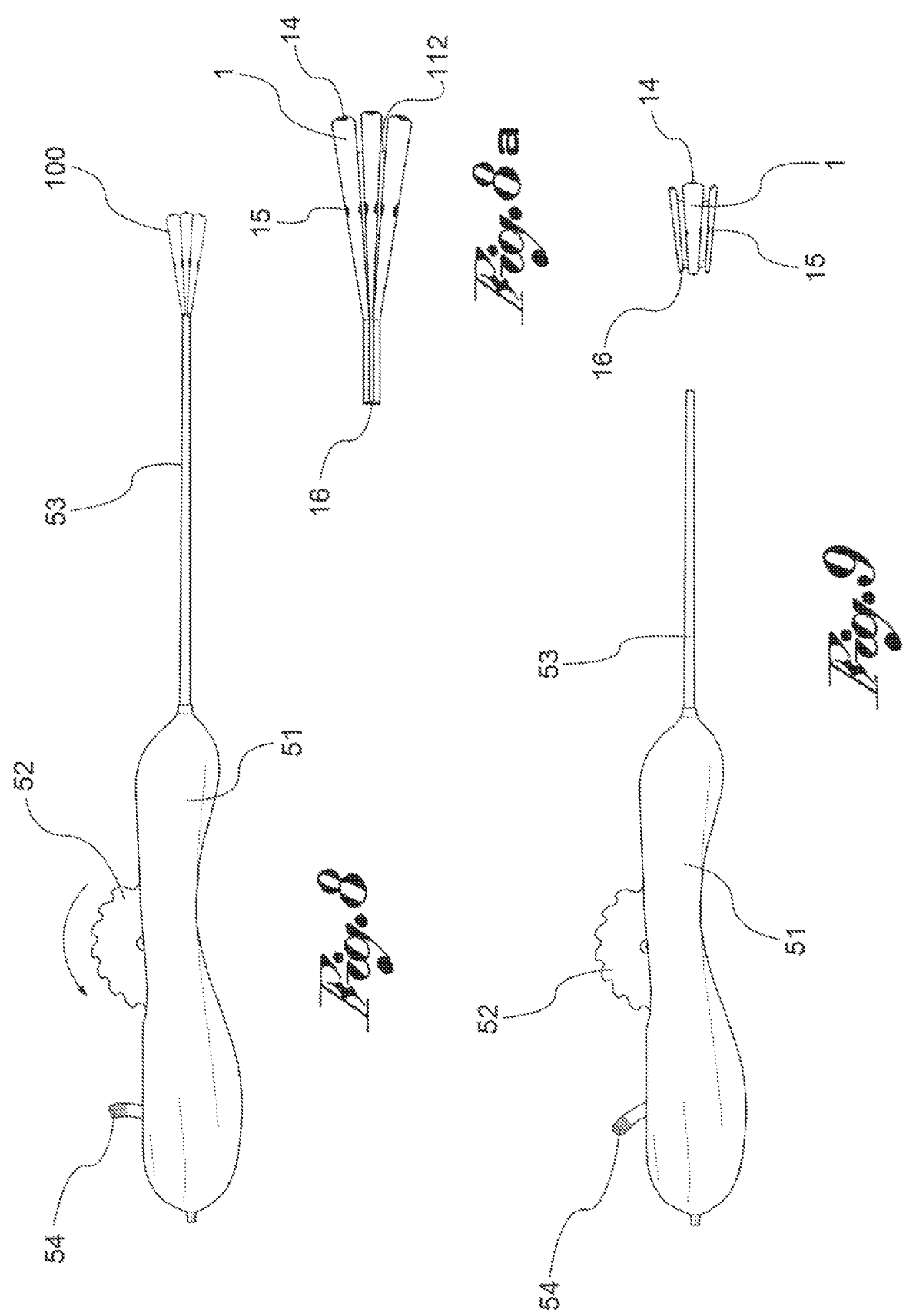

VENOUS ENDOLUMINAL DEVICES FOR THE TREATMENT OF DEFECTS OF VEINS

CROSS-REFERENCE TO RELATED APPLICATIONS

This application is a National Phase application of PCT International Application No. PCT/IB2013/056283, International Filing Date, Jul. 31, 2013, claiming priority to Italian Patent Application No. BS2012A000154, filed Oct. 30, 2012, and Italian Patent Application No. BS2013A000080, filed May 30, 2013, each of which is hereby incorporated by reference in its entirety.

FIELD OF THE INVENTION

The present invention relates to an endovascular device for treating endoluminal anomalies of the inner jugular vein.

BACKGROUND OF THE INVENTION

Such endoluminal anomalies may present in the form of septums or membranes varying in thickness and malfunctioning valve anomalies varying greatly in form, direction and motility. Such endoluminal defects of a probable congenital nature are habitually located in the section of inner jugular vein next to its junction with the subclavian vein and thus of its outlet into the brachiocephalic vein. The proximal section of the inner jugular vein is characterised by a junctional area having a diameter varying from 8 to 12 mm and a physiological dilation of the vein overlying the junctional area defined as the "bulb".

Valve anomalies of the inner jugular vein determine a slowing down, of variable entity, of the venous outflow from the brain to the heart. In particularly serious cases, the venous outflow coming from the brain is blocked, and can only flow out through compensatory collateral circles.

The inner jugular vein being the main path of venous outflow of the brain in a supine position, it is evident that a severe alteration of the venous outflow may determine a serious clinical condition.

The morphological and haemodynamic alterations described above have been found in many patients with chronic neurodegenerative disease such as multiple sclerosis.

The venous endoluminal device according to the present invention is of the permanent type designed for treatment of the endovascular defects of the inner jugular veins typical of patients suffering from delayed cerebral venous outflow.

Recent developments in the medical field have led to the application and diffusion of dilatory angioplasty for the treatment of endoluminal defects of the inner jugular veins.

The results of dilatory angioplasty applied to the treatment of such defects are very controversial and characterised by a non-satisfactory immediate haemodynamic and/or morphological result. In addition, a high incidence of precocious restenosis has been observed and, to a lesser extent, obstructions and thromboses of the jugular vein.

The use of arterial endoluminal devices of the permanent type (such as stents) has been experimented as an alternative to dilatory angioplasty.

In this case too results have been disappointing, so much so as to lead to the complete abandonment of these devices. The main complications recorded in relation to arterial stents applied in venous sites are the migration of the stent and the precocious restenosis due to myointimal hyperplasia, and finally the more or less complete thrombosis of the stent.

Such precocious and delayed complications of the stents used today are mainly due to the construction principle of the aforesaid devices. Briefly, such devices are designed to exert a uniform and continuous radial force on the vessel wall. Specifically, they cause a permanent dilation with consequent loss of the physiological compliance of the venous wall. In addition, as a result of the constant trauma, an inflammatory phenomenon is triggered named myointimal hyperplasia which causes a fibrosis of the venous wall encompassing the stent and thereby occluding it.

Given the limited success of these methods, using devices designed for the treatment of arterial diseases, new endoluminal devices of the permanent type have recently been designed with specific characteristics for the treatment of defects of the jugular veins.

An example of such devices is disclosed in the document US2012/0130468, in which an implantable device for the support of a valve prosthesis is described. Such device, shown in FIG. 10B of this document, comprises a first portion and a second portion joined by axial elements and positioned astride the valve to be treated.

A further example of such devices is disclosed in the document US2012/0046731, in which a stent able to support and conform the vessel in which it is implanted is described. Such stent, shown for example in FIG. 38 of this further document, comprises a distal ring and a proximal ring joined by flexible axial elements.

The known devices, despite having been specifically designed for treatment of the defects of the jugular veins have a number of drawbacks, such as not ensuring a minimum radial force on the walls of the vessels and minimal construction material inside the body without the risk of migration of the device.

SUMMARY OF THE INVENTION

The purpose of the present invention is to resolve the drawbacks of the prior art bearing in mind the needs of the sector.

Such purpose is achieved by venous endoluminal devices and methods for the treatment of defects of veins, as described and claimed herein.

The characteristics and advantages of devices and methods according to the present invention are evident from the description below and as illustrated in the drawings briefly described below.

BRIEF DESCRIPTION OF THE FIGURES

FIGS. 6 to 9 show the release steps of an endoluminal device according to the present invention;

FIGS. 7 and 8 show in detail the configuration adopted by the endoluminal device of FIGS. 7 and 8 during the release steps;

DETAILED DESCRIPTION

Figure 4:
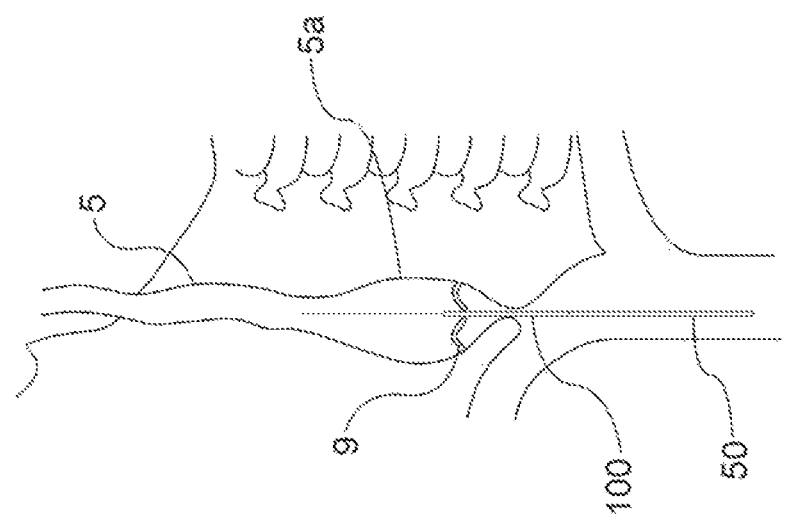
FIG. 4 shows a positioning step of the endoluminal device inside the venous system, in a compressed configuration, according to the present invention.
Figure 3:
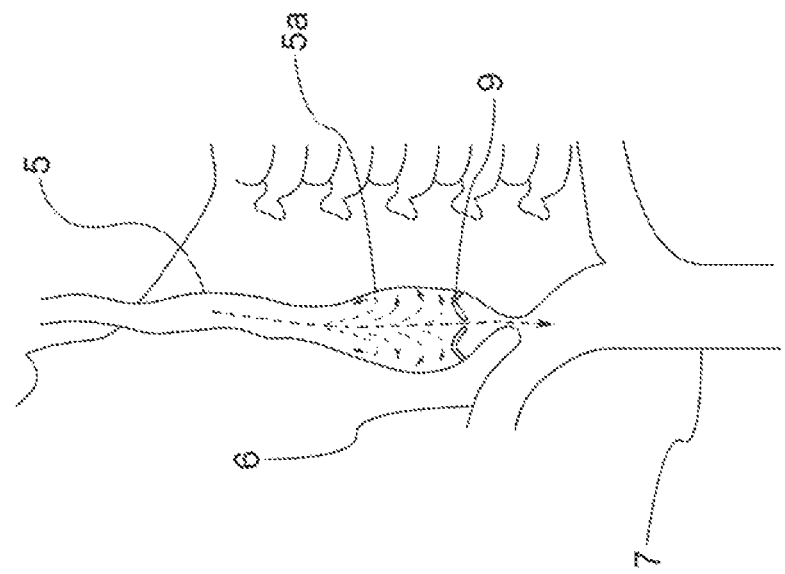
FIG. 3 shows a simplified diagram of the vascular venous system leading to the brain.

With reference to the appended drawings, and in particular to FIG. 4, a simplified diagram of the vascular venous system in outflow from the brain is illustrated. In particular, the venous flow is conducted through the inner jugular vein 5, which together with the subclavian vein 6, leads to the brachiocephalic vein 7. The extra cranial venous vascular system described above is characterised by the presence of a series of valves, such as the valve 9 in the right inner jugular vein 5.

As mentioned above, the junctional iuxta section of the inner jugular vein is often the seat of valve malformations, septums and membranes.

One example of such defects is shown again in FIG. 4, in which an anomalous dilation 5a is present in the inner jugular vein 5, in the cranial direction with respect to an endoluminal defect 9 which causes a delayed outflow of the blood and consequent reflux (shown by the dotted lines). To correct the defects of the inner jugular veins, a venous endoluminal device 100 is used, as shown in the appended drawings.

The endoluminal device 100 has a compressed configuration, for loading onto a specific release device 50 and for its subsequent insertion and positioning inside the vein to be treated. The endoluminal device 100 also has an expanded configuration, for the treatment of an endoluminal defect.

The endoluminal device 100 is provided with a substantially tubular body 10 which defines an inner lumen.

Preferably, the body 10 is a truncated-conical shape, as shown in FIG. 9. In particular, in an expanded configuration, the endoluminal device 100 has a diameter which varies from 10 to 16 millimetres at the lesser proximal base and from 12 to 20 millimetres at the greater distal or cranial base, and a length of approximately 28 mm.

Figure 1:
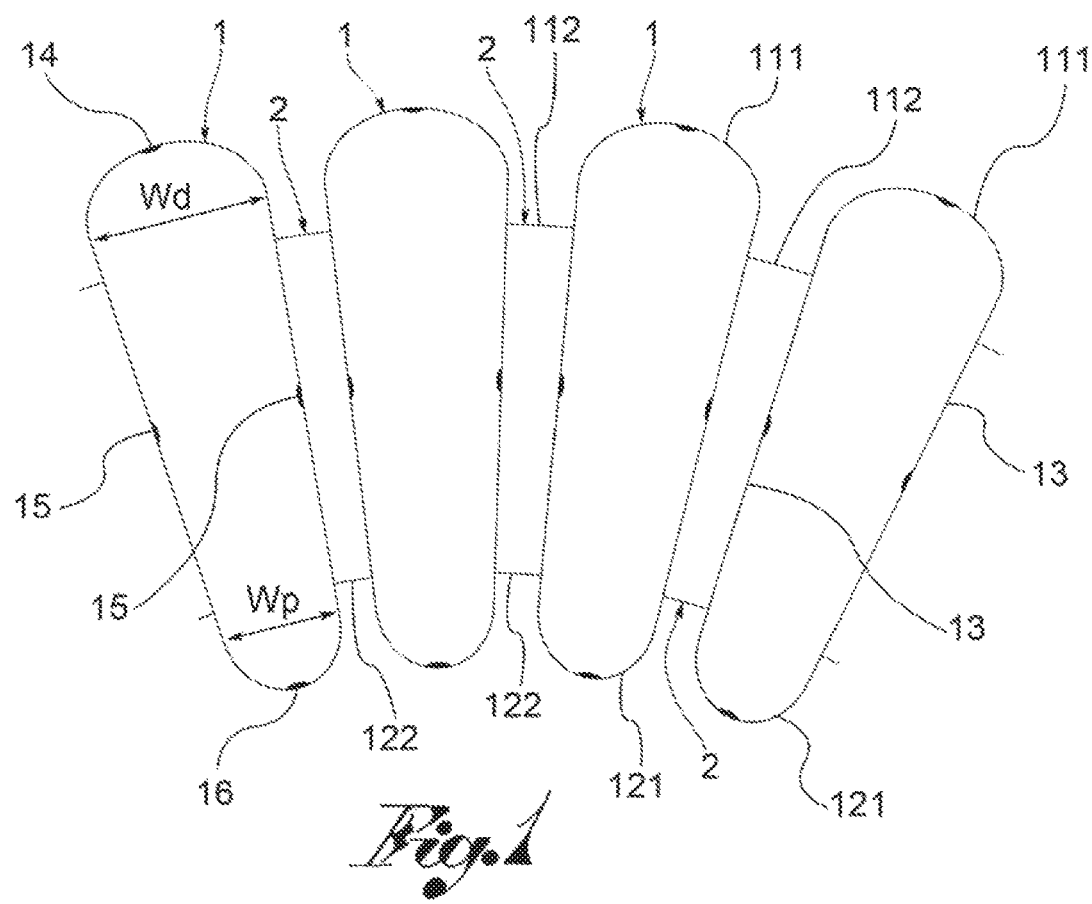
FIG. 1 shows a view of a venous endoluminal device, open and flattened, according to the present invention.

The endoluminal device 100, shown in detail in FIG. 1, comprises support modules 1 joined by transversal bridges 112.122.

The support module 1 has a distal radial width Wd and a proximal radial width (Wp). In particular, the proximal radial width Wp is less than the distal radial width Wd.

Preferably, the support module 1 has a shape similar to that of a petal.

The configuration of the support modules 1, wider in a distal direction and narrower in a proximal direction, gives the endoluminal device 100 a truncated conical shape. In use, the truncated conical shape of the body 10, positioned with its greater cross-section facing the brain, makes it possible to prevent the migration of the endoluminal device 100 towards the heart.

In detail, the support module 1 comprises a proximal section 121, projecting from the proximal bridges 122, and a distal section 111, projecting from the distal bridges 112. Preferably, the proximal section 121 and the distal section 111 are substantially U-shaped. In addition, the support module 1 comprises two longitudinal elements 13 placed so as to connect the distal section 122 to the proximal section 121.

In addition, the transversal bridges 122,112 form connection cells 2 between the support modules 1. Preferably, the connection cell 2 also has a proximal radial width Wp less than the distal radial width Wd.

The endoluminal device 100 is thus provided with cells having different geometries (FIG. 1). In particular, the cells comprise:
a plurality of support modules 1, and
a plurality of connection cells 2, defined between the bridges 112, 122 and the longitudinal elements 13.

Preferably, the support modules 1 and the connection cells 2 alternate in a radial direction along the body 10.

Preferably, each support module 1 has a proximal radial width Wp less than the distal radial width Wd.

Even more preferably, each connection cell 2 has a proximal radial width Wp less than the distal radial width Wd.

Preferably, the support modules 1 extend along the entire length of the body 10.

Such configuration of the support modules 1 makes it possible to exert a minimal radial force on the walls of the vein 5. In use, the endoluminal device does not need to exert a great radial force, which in the short term would cause the obstruction of the stent as a result of myointimal hyperplasia, since it only needs to make the endoluminal defects adhere to the venous wall. In the case in point, a minimal radial force which corrects the endoluminal defect of the vein and which does not damage the venous walls is sufficient.

Such configuration of the support modules 1 furthermore permits an endoluminal device with very wide meshes to be obtained, thereby reducing the quantity of material implanted inside the vein.

Preferably, the support modules 1 are a convex shape. In addition, the support modules 1 are empty, that is to say without bridges or other internal elements, Such configuration of the support modules 1 avoids the presence of projections or protuberances which could catch on or penetrate the vessel wall and cause lesions and restenosis.

In a preferred variant, shown in FIG. 1, the support modules 1 are four in number and are angularly equidistant in a radial direction.

Preferably, the support modules 1 are bigger than the connection cells 2. In particular, the support modules 1 extend beyond the connection cells 2 in a distal direction and/or in a proximal direction. Such configuration helps to reduce the quantity of material inside the vein.

In addition, the bridges are distal bridges 112 and proximal bridges 122. Preferably, the distal bridges 112 are longer than the proximal bridges 122. Such configuration of the bridges 112,122 contributes to the truncated conical shape of the endoluminal device 100. In particular, for the same modules and cells, by modifying the length of the bridges 112, 122, it is possible to modify the conicity of the truncated conical body 10.

Preferably, the bridges 112,122 are substantially curved.

The body 10 is made from self-expanding material, preferably from nitinol. The body 10 is made by laser cutting or wound filament.

Figure 2:
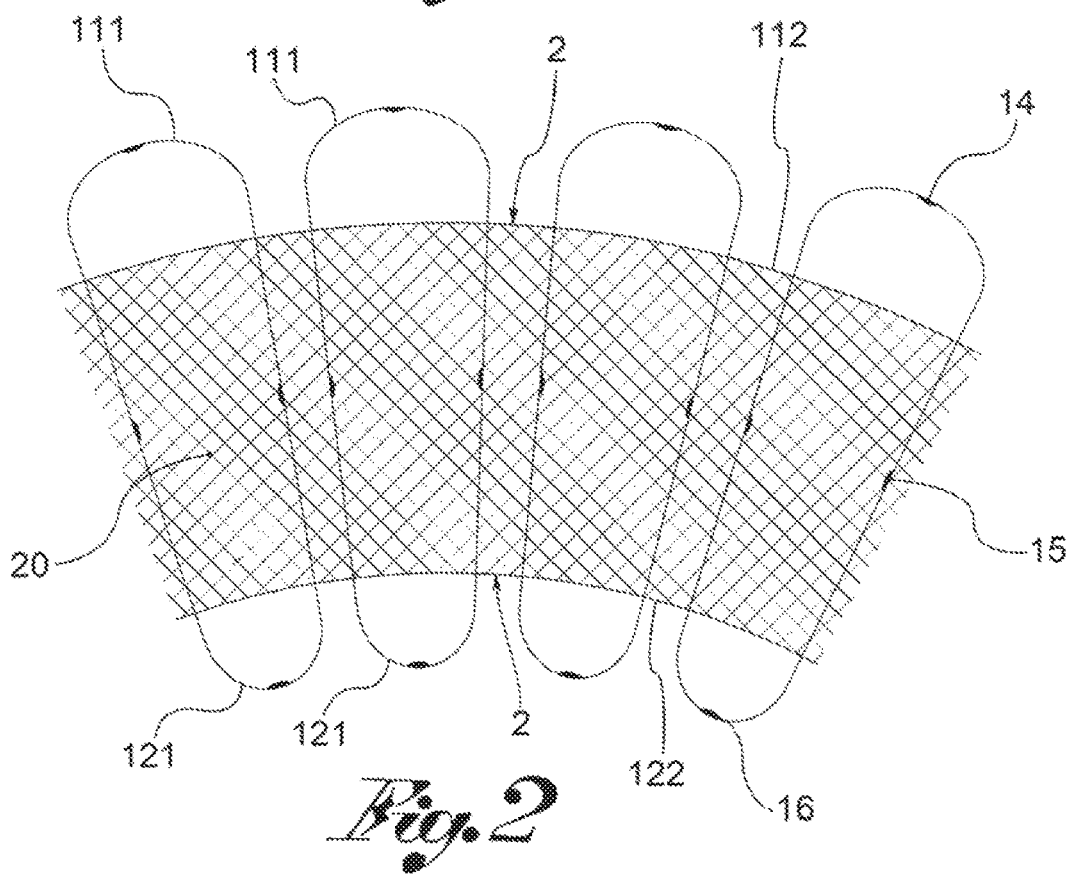
FIG. 2 shows the device in FIG. 1, in an embodiment variant.
Figure 5:
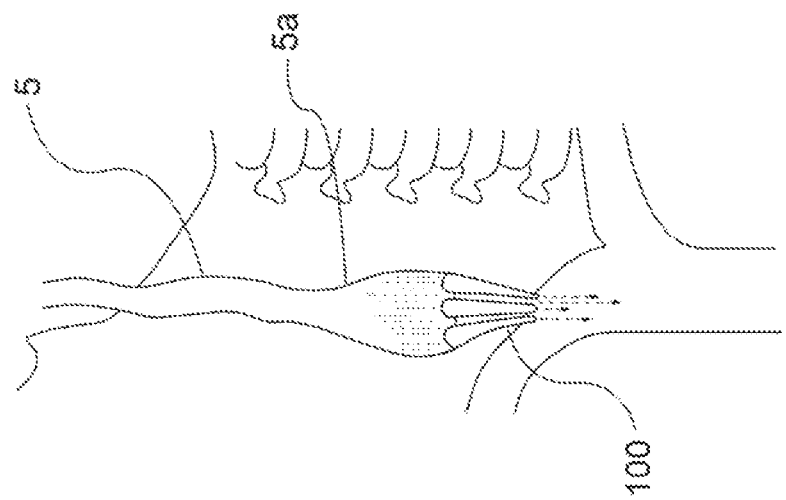
FIG. 5 shows an endoluminal device according to the present invention, in an expanded configuration positioned inside the venous system.

In one embodiment variant, shown in FIG. 2, the body 10 is covered at least partially by a mesh 20. Preferably, the connection cells 2 are completely covered by the mesh 20 and the support modules 1 are partially covered by the mesh 20. Preferably, the support modules 1 are completely covered by the mesh 20 except for the sections of cell 111,121 extending beyond the bridges 112,122.

Such mesh 20 is made from reabsorbable material. In particular, the mesh 20 forms an outer mesh covering with reabsorbable filament 5/0. Such outer covering 20 favours the adhesion of the endoluminal defects to the venous wall.

In addition, the endoluminal device 100 is provided with radio opaque markers 14, 15, 16. Preferably, each support module 1 is provided with a distal marker 14, a proximal marker 16 and two intermediate markers 15. In particular, the distal marker 14 is at the centre of the distal section 111, the proximal marker 16 is at the centre of the proximal section 121, and the intermediate marker 15 is at the centre of the longitudinal element 13.

Figure 10:
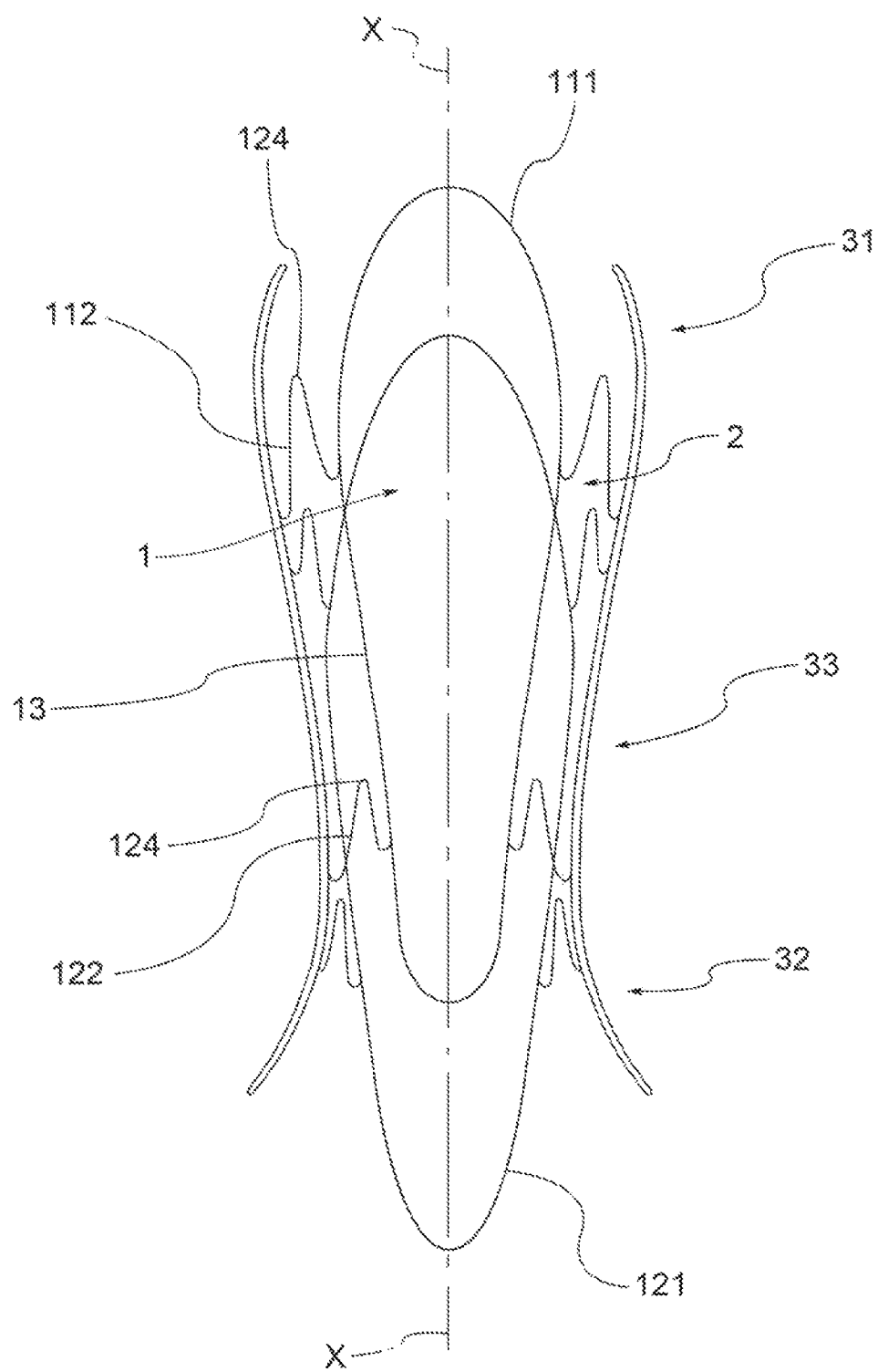
FIG. 10 shows an axonometric view of an endoluminal device according to the present invention, in a further embodiment variant.

In a further embodiment variant, shown in FIG. 10, the endoluminal device 100 is fitted with a body 10, preferably having a truncated conical shape at both ends, substantially an hour-glass shape, which defines an inner lumen.

The body 10 extends mainly in the direction of the length, along the axis X. A longitudinal direction along the axis X is thus defined and a radial direction substantially orthogonal to the axis X.

Preferably, the body 10 of the endoluminal device 100 is provided with a distal end 31, a proximal end 32 and a central portion 33.

Preferably, the central portion 33 is a truncated conical shape, with a greater diameter in a distal direction. Preferably, the distal end 31 continues with the same conicity as the central portion 33. Preferably, the proximal end 32 continues with the opposite conicity to the central portion 33.

Preferably, the distal end 31 has a maximum diameter which is greater than the maximum diameter of the proximal end 32.

In the expanded configuration, the endoluminal device 100 has a diameter which varies from 10 to 16 millimetres at the proximal end 32, and from 12 to 20 millimetres at the distal or cranial end 31, and a length of approximately 32 mm. The endoluminal device 100 thus maintains a certain overall truncated conicity.

The endoluminal device 100 comprises support modules 1, oriented longitudinally, joined by transversal bridges 112,122. Preferably therefore, the support modules 1 extend along the direction of the axis X.

Preferably, the support modules 1 are four in number and are angularly equidistant in a radial direction.

Preferably, the proximal radial width Wp is less than the distal radial width Wd. Such configuration of the support modules 1, wider in a distal direction and narrower in a proximal direction, gives the endoluminal device 100 a shape having a varying diameter.

The support modules 1, preferably consisting of a single Nitinol filament, are internally empty, that is to say without bridges or other internal elements. In addition, the support modules 1 extend along the entire longitudinal length of the body 10. Such particular configuration of the device 100 provides a support to the venous walls making the endoluminal defects adhere to the wall, but does not determine a permanent dilation of the vein in that it enables the venous walls to collapse, at least partially, inside the support modules, thus adapting to the normal and physiological variations in diameter of the vein.

The support modules 1 are joined to each other in a radial direction to form the body 10 by means of transversal bridges 112,122, positioned rearwards of the ends 31, 33.

Preferably, the distal bridges 112 are positioned in the area where the distal portion 31 and the central portion 33 join. Preferably, the proximal bridges 122 are positioned in the area where the proximal portion 32 and the central portion 33 join.

As shown in the drawings, each pair of support modules 1 is joined by a distal bridge 112 and a proximal bridge 122.

Preferably, the distal bridge 112 is longer than the proximal bridge 122. This way, for the same modules and cells, by modifying the length of the bridges 112, 122, it is possible to modify the conicity of the body 10.

Preferably, the bridges 112,122 have a substantially V-shape or gull wing shape. In a preferred variant, the distal bridges 112 and the proximal bridges 122 are positioned so that the summit 114, 124 of the V is oriented towards the central portion 33. In a further variant, the distal bridges 112 and the proximal bridges 122 are positioned so that the summit 114, 124 of the V is oriented in the same longitudinal direction, for example towards the distal portion 31 or towards the proximal portion 32.

In addition, the transversal bridges 122,112 form connection cells 2 between the support modules 1. Preferably, the connection cell 2 also has a proximal radial width Wp less than the distal radial width Wd.

Preferably, the distal section 111, projecting from the distal bridges 112, of each support module 1, is at least partially projecting in a radial direction, internally in relation to the inner lumen of the body 1. Such configuration reflects the shape of the venous site which the endoluminal device 100 is positioned in. The distal section 111 in fact positions itself at the bulb of the inner jugular, resting on the venous walls without deforming them.

Preferably, only the distal end of each support module is curved on the inside. The presence of curved ends internally, prevents portions of the endoluminal device from catching on the venous walls and damaging them.

Preferably, the proximal section 121, projecting from the proximal bridges 122, of each support module 1, is at least partially projecting in a radial direction, outwardly in relation to the inner lumen of the body 1. Preferably, only the proximal end of each support module is curved on the outside.

Such configuration makes it possible for the endoluminal device 100 to get a partial hold on the walls of the brachiocephalic vein preventing its migration in a cranial direction. The proximal section 121 in fact positions itself proximally in the brachiocephalic vein, as well as physiologically narrowing the junctional area, acting as an anchor for the endoluminal device 100 without damaging the venous walls.

Preferably, the proximal section 121 and the distal section 111 are substantially U-shaped. In addition, the support module 1 comprises two longitudinal elements 13 placed so as to connect the distal section 122 to the proximal section 121.

The distal sections 111, 121, and in particular the ends of the support modules 1 of the device 100, extend in opposite directions, beyond the connection bridges 112, 122, respectively in a distal direction and in a proximal direction.

Preferably, the distal sections are free of interconnections. Such configuration helps to ensure a greater flexibility of the device and thus permits extensive adjustment capacities to the variations of calibre of the vein.

Preferably, each support module 1 is provided with a distal marker 14, a proximal marker 16 and two intermediate markers 15. In particular, the distal marker is at the centre of the distal section 111, the proximal marker 16 is at the centre of the proximal section 121, and the intermediate marker 15 is at the centre of the longitudinal element 13. Such arrangement of the markers permits the accurate positioning of the endoluminal device 100 inside the vein to be treated The present invention also relates to a venous endoluminal catheter comprising an endoluminal device 100 and a release system 50 for the positioning and release of the endoluminal device 100 in an expanded position inside the venous vessel to be treated, shown in FIGS. 6 to 9.

The release system 50 is provided with a double lock and permits recovery of the endoluminal device 100 in the case of incorrect positioning.

The release system 50 comprises a grip 51 fitted with a wheel 52 for moving back the outer sheath 53 and a locking lever 54.

FIG. 6 shows the release system 50 completely closed, with the endoluminal device 100 completely compressed (FIG. 6a) between the outer sheath 53 and the inner tube (not shown). The lever 54 is in a first closed configuration, in which the wheel 52 cannot be rotated and the sheath 53 cannot therefore be moved backwards to release the device 100.

FIG. 7 shows the release system 50 partially open, with the endoluminal device 100 partially compressed between the outer sheath 53 and the inner tube (not shown) and partially expanded. In particular, as shown in FIG. 7a, the endoluminal device 100 is compressed in the portion comprised between the proximal marker 16 and the intermediate marker 15, and expanded in the portion comprised between the intermediate marker 15 and the distal marker 14. The lever 54 is in a first locked configuration, in which the wheel 52 cannot be rotated further and the sheath 53 cannot therefore be moved further backwards to continue the release of the device 100.

FIG. 8 shows the release system 50 almost completely open, with the endoluminal device 100 almost completely expanded. In particular, as shown in FIG. 8a, the endoluminal device 100 is compressed only for a small proximal portion between the proximal marker 16 and the intermediate marker 15. The lever 54 is in a second locked configuration, in which the wheel 52 cannot be rotated further and the sheath 53 cannot therefore be moved definitively backwards to fully release the device 100.

The release system 50 permits recovery of the endoluminal device 100 in the case of incorrect positioning. In fact, when the release system 50 is partially open (FIG. 7) or almost completely open (FIG. 8) it is still possible, by rotating the wheel 52 in an opposite direction and thus moving the sheath 53 forwards, to recapture the device 100 compressing it under the sheath 53 once again.

FIG. 9 shows the release system 50 completely open, with the endoluminal device 100 completely expanded. The lever 54 is in an open configuration, in which the wheel 52 can be moved back as far as the complete release of the device 100.

The present invention also relates to a method for the treatment of defects of the veins, comprising the steps of:
  providing a venous endoluminal catheter comprising an endoluminal device 100 and a release system 50;
  inserting the endoluminal catheter inside the vein 5 to be treated;
  partially releasing the endoluminal device 100 as far as a first locking and exact positioning at the point of the defect;
  almost total releasing the endoluminal device 100 and verifying its adhesion to the wall of the vein;
  totally releasing the endoluminal device 100.

In particular, the step of inserting the endoluminal device comprises the following sub-steps:
  a) cannulation of the vein by means of a guide wire 51 and specific catheter;
  b) diagnostic phlebography aimed at localising the site of the defect and extent of delay of the flow.
  c) positioning of the endoluminal catheter in such a way that the endoluminal device 100 is next to the defect of the vein.

Preferably, the endoluminal device 100 is positioned in the area where the inner jugular vein joins the subclavian vein.

In addition, in the case of incorrect positioning of the endoluminal device 100, the method provides for the recovery of the endoluminal device 100, as an alternative to its definitive release.

Innovatively, a venous endoluminal device according to the present invention makes it possible to correct vein defects without damaging the vessel wall.

Advantageously, the truncated conical shape of the endoluminal device prevents the migration of the stent towards the heart.

Advantageously, the particular shape of the cells and of the modules avoids the presence of projections or protuberances which could catch on or penetrate the vessel wall and cause lesions and restenosis.

Advantageously, the particular shape of the cells and of the modules makes it possible to make the endoluminal defects adhere to the venous wall exerting a minimal radial force.

Advantageously, the particular shape of the cells and of the modules makes it possible to obtain a very wide mesh device, to leave as little material as possible inside the vein.

Advantageously, the presence of the outer covering around the body of the endoluminal device favours the adhesion of the endoluminal defects to the venous wall.

Advantageously, the truncated conical shape of the endoluminal device, similar to an hour-glass, simultaneously prevents the migration of the endoluminal device towards the heart and towards the brain.

Advantageously, the proximal ends facing outwards are an advantageous element for preventing the migration of the endoluminal device towards the brain.

Advantageously, the particular configuration of the device, having variable diameter and longitudinal (as opposed to radial) force, respects the physiological elasticity of the venous wall and adjusts to the variations in diameter of the veins.

Advantageously, the presence of support modules which extend in a longitudinal direction, and thus suitable to exert a longitudinal and not a radial force, prevents excessive dilation of the vessel and its possible rupture.

Advantageously, an endovascular device according to the present invention is particularly suitable for treating endoluminal anomalies of the inner jugular vein and of the larger veins of the thorax and abdomen, in that it respects the physiological compliance of the venous wall. The venous wall has in fact a strong elastic component which permits said vein to adapt, modifying its diameter, to pressure, postural and mechanical variations. In addition, evident variations of the diameter of the vein may be observed following normal or forced respiration. Traditional arterial stents applied in venous sites exert a uniform and continuous radial force on the venous wall which causes a permanent dilation with loss of the physiological compliance of the vein and a consequent inflammatory phenomenon named myointimal hyperplasia which causes a fibrosis of the venous wall encompassing the stent and thereby occluding it. The endovascular device according to the present invention has not been designed to keep a vessel constantly dilated but to adapt to the normal and physiological variations in diameter of the vein. In fact, the particular configuration of the device does not determine a permanent dilation of the vein, but provides a support for the venous walls which are in any case free to collapse inside the support modules.

In particular, the advantageous aspect of the present device is based on the following concepts:

1) Configuration of the Device

The device has a particular truncated conical shape with the larger base facing towards the cranium. This configuration is an essential element for preventing the migration of the device towards the heart chambers. The "petal" shaped support modules are connected by bridges of variable length so as to contribute to the truncated conical configuration of the device. In fact the variation of the length of the bridges makes it possible to modify the truncated conical configuration of the device.

2) Minimum Radial Force

The device has been designed to make the endoluminal defects adhere to the wall of the inner jugular vein. Thanks to the particular configuration described above, the device will exert a minimum radial force on the wall of the vein. In addition, the shape of the modules free of any projecting or pointed parts together with the minimal radial force prevents the excessive dilation of the vessel and its possible rupture.

3) Minimum Construction Material of the Device

The minimal presence of construction material of the device in contact with the wall of the jugular, significantly limits the myointimal hyperplasia typical of arterial stents. Having to treat relatively young patient, with a long life expectancy, this particular construction ensures that the device remains patent for a long period.

4) Configuration of the Support Modules

The support modules, preferably 4 in number and extending along the entire longitudinal length of the device, by being internally empty, permit the partial collapse of the venous wall towards the inside of the vessel thus contributing to maintaining the physiological compliance of the venous wall.

It is clear that a person skilled in the art may make certain modifications to the devices described and claimed herein without departing from the scope of protection of the present invention.

The invention claimed is:

1. An endoluminal venous stent, comprising:
   a tubular body, the tubular body defining an unobstructed inner lumen and four support modules joined by transversal bridges, wherein an inner passage radially inward from the support modules and the transversal bridges is free of obstructions extending radially across the inner passage;
   wherein the support modules have a proximal radial width less than a distal radial width;
   wherein the support modules extend along an entire length of the tubular body;
   wherein each of the support modules has a closed convex shape defining an internal area free of bridges or other internal elements, to enable a partial collapse of venous walls towards the inner lumen of the tubular body and to maintain physiological compliance of a vein; and
   wherein the support modules are angularly equidistant from each other in a radial direction.

2. The stent of claim 1, wherein the tubular body comprises a truncated cone.

3. The stent of claim 1, wherein the tubular body defines the inner lumen and the support modules are oriented longitudinally and joined, at a distal end, by distal bridges and at a proximal end, by proximal bridges, wherein each support module comprises a distal section, extending in a distal direction beyond the distal bridges and wherein the distal section is at least partially projecting in a radial direction, internally in relation to the inner lumen of the body.

4. The stent of claim 3, wherein the tubular body comprises:
   a truncated conical central portion, with a greater diameter in a distal direction, and
   a truncated conical distal end, having a same conicity as the central portion,
   wherein the conicity is a ratio between a difference in diameters of two sections of a cone and an axial distance between the two sections of the cone, and
   wherein the distal bridges are positioned in an area where the distal portion and the central portion join.

5. The stent of claim 4, wherein the tubular body further comprises a truncated conical proximal end having an opposite conicity to the central portion, and wherein the proximal bridges are positioned in an area where the truncated conical proximal end and the truncated conical central portion join.

6. The stent of claim 5, wherein a periphery of the stent from the truncated conical distal end to the truncated conical central portion to the truncated conical proximal end comprises an uninterrupted curving surface.

7. The stent of claim 3, wherein each support module comprises a proximal section, extending in a proximal direction beyond the proximal bridges, wherein the proximal section is at least partially projecting in a radial direction, externally in relation to the inner lumen of the body.

8. The stent of claim 3, wherein the tubular body has a truncated conical shape at both ends and has an hour-glass shape.

9. The stent of claim 3, wherein the transversal bridges have a substantially V-shape or gull wing shape.

10. The stent of claim 1, wherein the tubular body defines an inner lumen and the support modules are oriented longitudinally and joined, at a distal end, by distal bridges and at a proximal end, by proximal bridges, wherein each support module comprises a proximal section, extending in a proximal direction beyond the proximal bridges, and wherein the proximal section is at least partially projecting in a radial direction, externally in relation to the inner lumen of the body.

11. The stent of claim 10, wherein each support module comprises a distal section, extending in a distal direction beyond the distal bridges, wherein the distal section is at least partially projecting in a radial direction, internally in relation to the inner lumen of the body.

12. The stent of claim 1, wherein the bridges comprise distal bridges and proximal bridges and wherein the distal bridges are longer than the proximal bridges.

13. The stent of claim 1, wherein the support modules are joined by transversal bridges so as to form a plurality of connection cells, wherein the support modules are larger than the connection cells.

14. The stent of claim 13, wherein the connection cells have a proximal radial width and a distal radial width, and the proximal radial width is less than the distal radial width.

15. The stent of claim 1, wherein the support modules extend beyond the connection cells in a distal direction and/or in a proximal direction.

16. The stent of claim 1, wherein the tubular body comprises self-expanding material.

17. The stent of claim 16, wherein the self-expanding material comprises nitinol.

18. The stent of claim 1, further comprising a positioning marker.

19. The stent of claim 1, further comprising:
a distal positioning marker;
a proximal positioning marker;
an intermediate positioning marker.

20. The stent of claim 1, further comprising:
a distal positioning marker at a center of an end of the distal section of one of the support modules;
a proximal positioning marker at a center of an end of the proximal section of one of the support modules;
an intermediate positioning marker at a center of an end of the intermediate section of one of the support modules.

21. The stent of claim 1, further comprising a release assembly for positioning and releasing the stent.

22. The stent of claim 21, wherein the release assembly comprises;
a grip;
an outer sheath;
a wheel engaging the outer sheath; and
a lever moving between a locked configuration in which the wheel cannot be rotated and an open configuration in which the wheel is movable.

23. The stent of claim 1, wherein only a proximal section of each support module curves radially outward; and wherein only a distal section of each support module curves radially inward.

* * * * *